United States Patent [19]

Aoki et al.

[11] Patent Number: 5,364,989
[45] Date of Patent: Nov. 15, 1994

[54] 1,1,1-TRICHLORO-2-NITROETHANE PRODUCTION

[75] Inventors: Isao Aoki, Daiwahigashi; Takanori Tabuchi, Osaka; Isao Minamida, Hyoge, all of Japan

[73] Assignee: Takeda Chemical Industries, Ltd., Japan

[21] Appl. No.: 908,725

[22] Filed: Jul. 6, 1992

Related U.S. Application Data

[63] Continuation of Ser. No. 527,898, May 24, 1990, abandoned, which is a continuation-in-part of Ser. No. 473,173, Jan. 31, 1990, abandoned.

[30] Foreign Application Priority Data

Jan. 31, 1989 [JP]   Japan ................................. 1-023356

[51] Int. Cl.$^5$ ................... C07C 205/02; C07C 201/06
[52] U.S. Cl. .................... 568/946; 568/924; 544/336; 546/304; 546/329; 548/193; 564/395
[58] Field of Search ................................ 568/924, 946

[56] References Cited

U.S. PATENT DOCUMENTS 4,518,812  5/1985  Baasner et al. ...................... 568/946
4,533,776  8/1985  Baasner et al. ...................... 568/946

FOREIGN PATENT DOCUMENTS 0302389  2/1989  European Pat. Off. ............ 546/331

OTHER PUBLICATIONS

Derwent Publications Ltd. J6 2048-681-A Abstract.
Chemical Abstracts, vol. 64, 1966, p. 8023.
Chemical Abstracts, vol. 53, 1959, p. 1111.
J. Org. Chem., vol. 25, Bachman et al., "Nitration Studies XII. Nitrohalogenation of Negatively Substituted Olefins with Mixtures of Dinitorgen Tetroxide and Halogens", 1960, pp. 1312–1323.
William A. Pryor, "Free Radicals" (McGraw-Hill Book Company, 1966), Halogenation by Bromine, pp. 189–190.
Buehler & Pearson, "Survey of Organic Synthesis", (1970, Wiley–Interscience, New York, London, Sydney, Toronto), pp. 357–358.
Isnikawa, "Synthesis and Function of Fluorine Compounds", pp. 15, 34, 35, 155, 156, 177, and English translation thereof, 1987 CMC Co. Tokyo.
Merck Index, Eleventh Edition, 1989, Nos. 4720, 4721 and 4723, pp. 759–760.

Primary Examiner—Alan L. Rotman
Attorney, Agent, or Firm—Wegner, Cantor, Mueller & Player

[57] ABSTRACT

Methods for the production of 1,1,1-trihalogeno-2-nitroethanes from 1,1-dihalogenoethylene by using nitric acid or its salt and hydrogen chloride or hydrogen bromide or its salt, and for the production of α-unsaturated amines from the 1,1,1-trihalogeno-2-nitroethanes which are useful as insecticides.

1 Claim, No Drawings

1,1,1-TRICHLORO-2-NITROETHANE PRODUCTION

This application is a continuation of U.S. application Ser. No. 07/527,898 filed May 24, 1990, now abandoned which is a continuation-in-part of Ser. No. 07/473,173, filed Jan. 31, 1990, now abandoned.

BACKGROUND OF THE INVENTION

1. Field of the Invention

The present invention relates to a process for the production of α-unsaturated amines. More particularly, it relates to an improved process for the production of α-unsaturated amines useful as insecticides and their intermediates of 1,1,1-trihalogeno-2-nitroethanes.

2. Description of the Prior Art

α-Unsaturated-amines of the formula (V) shown hereinbelow or their salts are excellent insecticidal compounds [cf. EP-302389A]. As intermediates for production of the same, 1,1,1-trihalogeno-2nitroethanes are known to be prepared by the methods of the following formulas [1] and [2].

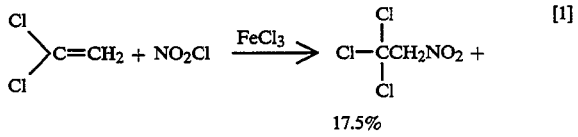

17.5%

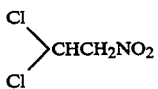

[cf. Izvest. Akad. Nauk S.S.S.R., Otdel. Khim. Nauk, 1958, 841 (C.A., 53, 1111i (1959))].

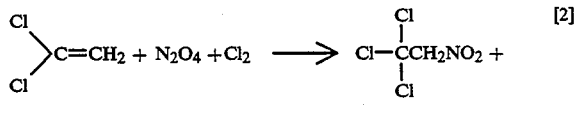

39.7%

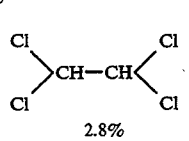

2.8%

However, the method of the formula [1] mentioned above which reacts 1,1-dichloroethylene with nitryl chloride shows the disadvantages that nitryl chloride is explosive [cf. Ber. 75 B, 1323(1942)]; its generation must use fuming nitric acid and chlorosulfonic acid which are dangerous and difficult to handle; a large amount of waste sulfuric acid must be disposed of and the yield of the object compound is low. The method of the formula [2] has many problems that very toxic dinitrogen tetroxide and chlorine gas must be used and the yield of the object compound is also low.

Also, the method of the formula [3] is known as the reaction of 1,1-dihalogenoethylene with nitric acid.

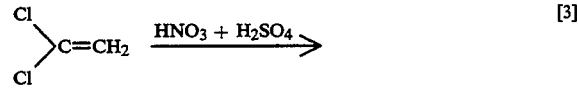

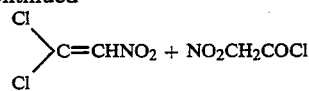

[cf. Probl. Organ. Sinteza. Akad. Nauk. S.S.S.R., Otd. Obshchi. Tekhn. Khim. 1965. 60 (CA. 64, 8023b (1966))]. However, it is reported that the yield of this reaction is extremely low, i.e., 10.6% of 1,1-dichloro-2-nitroethylene and 37% of nitroacetyl chloride, respectively.

On the other hand, the methods of the formulas [4] and [5] are known to introduce a nitro group and fluorine atom into 1,1-dihalogenoethylene (the latter is supposed to show reactivity entirely different from chlorine and bromine atoms).

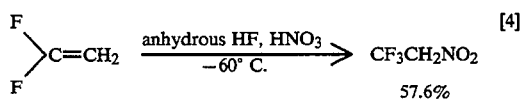

57.6%

[Izv. Akad. Nauk SSSR, Set. Kim., 1963, 1946(cf. CA. 60, 5325 g)]

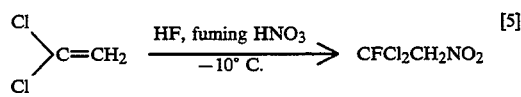

[Dokl. Akad. Nauk SSSR, 149, 330–333 (1963) (cf. CA. 59, 6215 g)]

Also, improvements on the above methods [4] and [5] are disclosed in DE 3,305,201 and DE 3,305,202, which however do not afford 1,1,1-trichloro or tribromo-2-nitroethane as the object compound and further do not suggest or teach to react olefins with hydrogen chloride or hydrogen bromide and nitric acid to introduce chlorine or bromine atom as well as nitro group.

The reaction of halogenated olefins with hydrogen chloride or hydrogen bromide requires use of a catalyst such as a metal chloride or active carbon, because their reactivity is less due to a reverse inductive effect (−I effect) of the halogen atom in the halogenated olefins. For instance, anhydrous ferric chloride is used in the reaction of 1,1-dichloroethylene with hydrogen chloride (cf. U.S. Pat. No. 2,209,000).

On the other hand, the reactivity of hydrogen fluoride is different from that of other hydrogen halides. For instance, hydrogen fluoride is required to react with common olefins under pressure, although they tend to react with hydrogen chloride or hydrogen bromide at room temperature [cf., J. Org. Chem., 3, 26(1938)]. Also, hydrogen fluoride is highly reactive with halogenated olefins, depending upon their structures [cf., J. Phys. Chem., 44, 275(1940)]. Specifically, it reacts easily, e.g. with 1,1-dichloroethylene at 65° C. [cf., J. Am. Chem. Soc., 65, 1271(1943)]. Further, hydrogen halide [HX; X=F, Cl, Br or I] is generally known as an electrophilic reagent. It is considered that in the addition reaction of olefin with hydrogen halide, ionized H+ initially attacks olefin and then X− reacts with carbonium cation formed as the intermediate. Hydrogen fluoride however reacts with a polyhalogenated olefin, with predominant nucleophilic attack of F−, thereby affording the desired product in good yield [J. Am. Chem. Soc., 82, 3091(1960)]. However, such nucleophilic reaction is not known for hydrogen chloride and hydrogen bromide. Accordingly, the reaction of 1,1-dihalogenoethylene with hydrogen chloride or hydrogen bromide whose reactivity is different from hydrogen fluoride is not suggested or predicted by the fact that 1,1-dihalogenoethylene as a kind of polyhalogenoolefin reacts easily with hydrogen fluoride.

Under these circumstances, the inventors of this invention have made various studies and have found unexpectedly the fact that when a 1,1-dihalogenoethylene is reacted with nitric acid or its salt and hydrogen chloride or hydrogen bromide or its salt, it provides at a high yield 1,1,1-trihalogeno-2-nitroethane (or 1-nitro-2,2,2-trihalogenoethane) in which a nitro group and a halogen atom are introduced at the same time and at the specific positions.

3. Summary of the Invention

This invention provides 1) a process for the production of 1,1,1-trihalogeno-2-nitroethanes which comprises reacting a 1,1-dihalogenoethylene of the formula (I):

wherein $X^1$ and $X^2$ are the same or different and represent a fluorine, chlorine, bromine or iodine atom, with nitric acid or its salt and hydrogen chloride or hydrogen bromide or its salt to obtain a compound of the formula (II):

wherein $X^1$ and $X^2$ have the same meanings as defined in the formula (I), and $X^3$ is chlorine or bromine atom;

2) a process for the production of α-unsaturated amines which comprises reacting a 1,1,1-trihalogeno-2-nitroethane of the formula (II) mentioned in the above 1) with an amino compound of the formula (III):

wherein $R^1$ is a hydrogen atom, an $C_{1-4}$ alkyl, halo-$C_{1-4}$alkyl, mono- or di-$C_{1-4}$alkoxy-$C_{1-4}$ alkyl, $C_{7-9}$aralkyl, optionally substituted phenyl, mono- or di-$C_{1-4}$alkylamino or $C_{1-4}$alkoxy group, A is a 3- or 4-pyridyl, pyrazinyl, 2-, 4- or 5-thiazolyl or phenyl group which may be substituted by a halogen atom or a $C_{1-4}$alkyl, $C_{1-4}$alkylthio or $C_{1-4}$alkoxy group, and n is 0, 1 or 2, or its salt and an amino compound of the formula (IV):

wherein $R_2$ is a hydrogen atom, or a $C_{1-4}$alkyl or $C_{7-9}$aralkyl group, $R_3$ is a hydrogen atom, a $C_{1-5}$alkyl, halo-$C_{1-4}$alkyl, hydroxy-$C_{1-4}$alkyl, mono- or di-$C_{1-4}$alkoxy-$C_{1-4}$alkyl, mono- or di-$C_{1-4}$ alkylthio-$C_{1-4}$alkyl, di-$C_{1-4}$alkylamino-$C_{1-4}$alkyl, tri-$C_{1-4}$-alkylsilyl-$C_{1-4}$alkyl, $C_{2-4}$alkenyl, $C_{7-9}$aralkyl, optionally substituted phenyl, amino, di-$C_{1-4}$ alkylamino, pyridyl-$C_{1-2}$alkyl or thiazolyl-$C_{1-2}$alkyl group (pyridyl and thiazolyl ring may be substituted by a halogen atom), or $R^2$ and $R^3$ together with the adjacent nitrogen atom may form a 5 or 6-membered heterocylic ring which may contain an oxygen atom or another nitrogen atom, or its salt, to obtain a compound of the formula (V):

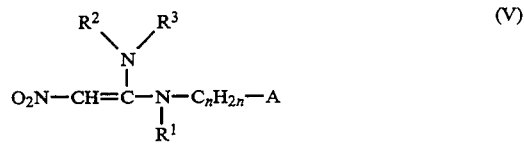

wherein $R^1$, $R^2$, $R^3$, A and n have the same meanings as defined above or its salt; and 3) a process for the production of α-unsaturated-amines which comprises treating a 1,1,1-trihalogeno-2-nitroethane of the formula (II) mentioned in the above 1) with a base to obtain a 1,1-dihalogeno-2-nitroethylene of the formula (VI):

wherein $X^4$ and $X^5$ are the same or different and represent a fluorine, chlorine, bromine or iodine atom, and then reacting it with an amino compound of the formula (III):

wherein $R^1$, A and n have the same meanings as defined in the above 2), or its salt and an amino compound of the formula (IV):

wherein $R^2$ and $R^3$ have the same meanings as defined in the above 2), or its salt to obtain a compound of the formula (V):

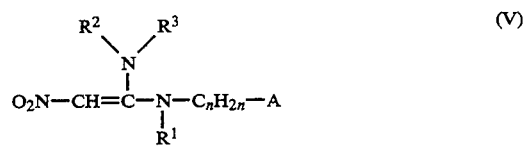

wherein $R^1$, $R^2$, $R^3$ A and n have the same meanings as mentioned above or its salt;

3. Preferred Embodiments of the Invention

With respect to $R_1$ of the above mentioned formulas, the $C_{1-4}$alkyl may be methyl, ethyl, n-propyl, i-propyl, n-butyl, i-butyl, s-butyl or t-butyl, among which methyl, ethyl or n-propyl is preferable;

the halo-$C_{1-4}$alkyl may be monochloromethyl, dichloromethyl, trichloromethyl, monofluoromethyl, difluoromethyl, trifluoromethyl, 2-chloroethyl, 2,2,2-trichloroethyl, 2-fluoroethyl, 2,2,2-trifluoroethyl or 1,1,2,2-tetrafluoroethyl;

the mono- or di-$C_{1-4}$alkoxy-$C_{1-4}$alkyl group may be methoxymethyl, dimethoxymethyl, ethoxymethyl, 1- or 2-methoxyethyl, 2,2-dimethoxyethyl, 3-methoxypropyl or 3,3-dimethoxypropyl, among which methoxymethyl, dimethoxymethyl, 2-methoxyethyl or 2,2-dimethoxyethyl is preferable;

the $C_{7-9}$aralkyl group may be benzyl, 4-chlorobenzyl, 4-bromobenzyl, 4-methylbenzyl, phenethyl or 4-methylphenethyl;

the optionally substituted phenyl group may be phenyl or a phenyl substituted by one to four substituents of a halogen (e.g., fluorine, chlorine, bromine or iodine), $C_{1-3}$alkyl (e.g., methyl, ethyl or propyl), $C_{1-3}$alkoxy (e.g., methoxy, ethoxy or propoxy), amino, hydroxy, carboxy or sulfo;

the mono- di-$C_{1-4}$alkylamino group may be methylamino, ethylamino, n-propylamino, i-propylamino or n-butylamino, or dimethylamino, methylethylamino, diethylamino or di-n-propylamino;

the $C_{1-4}$alkoxy group may be methoxy, ethoxy, n-propoxy, i-propoxy, n-butoxy or i-butoxy.

Preferable examples of $R^1$ are hydrogen atom and a $C_{1-4}$alkyl group such as methyl, ethyl or propyl.

With respect to $R^2$, the $C_{1-4}$alkyl group and $C_{7-9}$aralkyl group mentioned in $R^1$ are applicable to these groups of $R^2$. Preferable examples of $R^2$ are hydrogen atom and a $C_{1-4}$alkyl group such as methyl, ethyl or propyl.

With respect to $R^3$, the $C_{1-5}$alkyl group includes the $C_{1-4}$alkyl groups exemplified in $R^1$ and also amyl;

the halo $C_{1-4}$alkyl, mono- or di-$C_{1-4}$alkoxyalkyl, $C_{7-9}$aralkyl, optionally substituted phenyl and di-$C_{1-4}$alkylamino groups include the same ones exemplified in $R^1$;

the hydroxy $C_{1-4}$alkyl group may be hydroxymethyl, 1- or 2-hydroxyethyl, or 3-hydroxypropyl;

the mono- or di-$C_{1-4}$alkylthio-$C_{1-4}$alkyl group may be methylthioethyl, ethylthioethyl, n-propylthioethyl methylthiopropyl, dimethylthiomethyl, diethylthiomethyl, dimethylthioethyl or dimethylthiopropyl;

the di-$C_{1-4}$alkylamino-$C_{1-4}$alkyl group may be dimethylaminoethyl, diethylaminomethyl or dimethyl aminopropyl;

the tri-$C_{1-4}$alkylsilyl-$C_{1-4}$alkyl group may be trimethylsilylmethyl, trimethylsilylethyl, trimethylsilylpropyl, triethylsilylmethyl or tri-n-propylsilylmethyl;

the $C_{2-4}$alkenyl group may be vinyl, allyl or isopropenyl;

the pyridyl-$C_{1-2}$alkyl group may be substituted by one to three halogens (e.g., Cl, Br or F) on the pyridine ring and includes e.g., (3-pyridyl)methyl, (6-chloro-3-pyridyl)methyl, (6-fluoro-3-pyridyl)methyl, (6-bromo-3-pyridyl)methyl and 1-(3-pyridyl)ethyl;

the thiazolyl-$C_{1-2}$alkyl group may be substituted by one to three halogens (e.g., Cl, Br or F) on the thiazole ring and includes e.g., (2-thiazolyl)methyl, (5-thiazolyl)methyl, (2-chloro-5-thiazolyl)methyl, (2-bromo-5-thiazolyl)methyl, (4-thiazolyl)methyl and 1-(5-thiazolyl)ethyl. Preferable examples of $R^3$ are hydrogen, or a $C_{1-4}$alkyl such as methyl, ethyl or propyl.

The 5- or 6-membered heterocyclic group which may contain an oxygen atom and another nitrogen atom (in addition to the adjacent nitrogen atom to $R_2$ and $R_3$) may be pyrrolidino, piperidino, morpholino, or 4-methylpiperazino.

With respect to A, the 3- or 4-pyridyl, pyrazinyl, 2-, 4- or 5-thiazolyl or phenyl group may be substituted by one to four substituents of a halogen, $C_{1-4}$alkyl, $C_{1-4}$alkylthio or $C_{1-4}$alkoxy. Here, the halogen may be fluorine, chlorine, bromine or iodine, the $C_{1-4}$alkyl or $C_{1-4}$alkoxy includes the same groups exemplified in $R^1$ and the $C_{1-4}$ alkylthio may be methylthio, ethylthio, n-propylthio, i-propylthio, n-butylthio or i-butylthio. Examples of the 3- or 4-pyridyl groups which may be substituted are 3-pyridyl, 2- or 6-chloro-3-pyridyl, 5- or 6-bromo-3-pyridyl, 6-fluoro-3-pyridyl, 6-methoxy-3-pyridyl, 6-methyl-3-pyridyl, 5- or 6-trifluoromethyl-3-pyridyl, 2-methylthio-3-pyridyl, 2,6- or 5,6-dichloro-3-pyridyl, 4-pyridyl and 2,6-dichloro-4-pyridyl. Examples of the 2,4- or 5-thiazolyl groups which may be substituted are 2-thiazolyl, 4-thiazolyl, 5-thiazolyl, 2-chloro-5-thiazolyl, 2-bromo-5-thiazolyl, 2-fluoro-5-thiazolyl, 2-methyl-5-thiazolyl, 2-trifluoromethyl-5-thiazolyl, 2,4-dichloro-5-thiazolyl and 2-phenyl-5-thiazolyl. Examples of the pyrazinyl groups which may be substituted are 2-pyrazinyl, 5-chloro-2-pyrazinyl 5-bromo-2-pyrazinyl, 5-fluoro-2-pyrazinyl 5-methoxy-2-pyrazinyl and 5-methyl-2-pyrazinyl Examples of the phenyl groups which may be substituted are phenyl, p-chlorophenyl, p-bromophenyl, p-fluorophenyl, p-tolyl and p-methoxyphenyl.

Preferable examples of A are 2-halogeno-5-thiazolyl such as 2-chloro-5-thiazolyl and 6-halogeno-3-pyridyl such as 6-chloro-3-pyridyl.

A preferable example of $C_nH_{2n}$ is $CH_2$.

Specific examples of the 1,1-dihalogenoethylenes (I) which are the starting material of this invention are 1,1-difluoroethylene, 1,1-dichloroethylene, 1,1-dibromoethylene, 1,1-diiodoethylene, 1-chloro-1-fluoroethylene, 1-bromo-1-fluoroethylene, 1-fluoro-1-iodoethylene, 1-bromo-1-chloroethylene, 1-chloro-1-iodoethylene and 1-bromo-1-iodoethylene, among which 1,1-dichloroethylene is useful because it is commercially available at a low price.

According to this invention, a 1,1-dihalogenoethylene (I) is reacted with nitric acid or its salt and hydrogen chloride or hydrogen bromide (hereinafter sometimes referred to as hydrogen halide) or its salt to obtain a 1,1,1-trihalogeno-2-nitroethane (II). Each of nitric acid and hydrogen halide is generally used in 0.5 to 5 equivalents, preferably 1.0 to 2.0 equivalents, more preferably 1.2 to 1.5 equivalents to the compound (I). In case of using a salt of hydrogen halide, further addition of nitric acid enough to generate the hydrogen halide is desirable to give a good result. Similarly, when a salt of nitric acid is used, further addition of hydrogen halide which is necessary for generating nitric acid will achieve a good result. Examples of the salts of the hydrogen halides or nitric acid are the alkaline metal salts, alkaline earth metal salts, and ammonium salt. Needless to say, it is possible to use the mixture of nitric acid and its salt or the hydrogen halide and its salt. The hydrogen halide can be used as it is but is conveniently used as its aqueous solution which is easy to handle, i.e., as hydrohalogenic acid. The concentration of each of nitric acid and the hydrogen halide to be used in the reaction is suitably selected, as far as it does not impede the reaction. As nitric acid, 60% to 70% nitric acid which is available on the market or a fuming nitric acid can be used. About 35% hydrochloric acid and about 47% hydrobromic acid which are available on the market can be used as hydrogen chloride and hydrogen bromide, respectively. These hydrohalogenic acids and nitric acid can be used by diluting with water, although it may cause the delay of the reaction speed. The preferred initial concentration of each of the hydrogen halide and nitric acid to be added in the reaction system is about 40% to 60%.

The reaction is usually carried out in an aqueous system, to which an inert organic solvent may be added. Examples of the organic solvents are those which are not easily mixable with water, such as hydrocarbons (e.g., hexane, petroleum ether, ligroin, cyclohexane, benzene, toluene, or xylene), ethers (e.g., diethyl ether or diisopropyl ether), esters (e.g., ethyl acetate) or halogenated hydrocarbons (e.g., chloroform, dichloromethane, carbon tetrachloride, 1,2-dichloroethane or 1,1-dihaloethylene as the starting material); those which are homogenerously mixable with water, such as nitriles (e.g., acetonitrile), tetrahydrofuran (hereinafter referred to as "THF") or dioxane.

The reaction can be conducted at 0°-100° C. in a sealed vessel but be conducted at 0°-40° C., preferably 10°-35° C. in an open system. The reaction time is 5 minutes or more, preferably 0.5 to 48 hours. However, the reaction time of 5 minutes or more, preferably 0.5 to 5 hours is sufficient in case where the preferred concentrations of the hydrogen halide and nitric acid and the preferred reaction temperature are selected.

The order of addition of the raw materials, i.e., the compound (I), nitric acid or its salt and the hydrogen halide or its salt in the reaction system can be optionally determined. That is, to the mixture of two optional kinds of the raw materials can be added the remaining raw material, or to one optional raw material can be added the remaining two raw materials at the same time. Alternatively, the three raw materials can be simultaneously mixed. We found the fact that nitric acid is reacted with the 1,1-dihalogenoethylene to produce the 1,1,1-trihalogeno- 2-nitroethane. For instance, when 1,1-dichloroethylene is reacted with 70% nitric acid, it affords the mixture of 1,1,1-trichloro-2-nitroethane and 1,1,1,2-tetrachloroethane as main products, which however is not satisfactory for yield. On the other hand, hydrochloric acid or hydrobromic acid is hardly reacted with the 1,1-dihalogenoethylene under the condition of the present invention. Thus, it will be understood that in accordance with the reaction of the present invention, the coexistence of nitric acid and the hydrogen halide is required to prepare the 1,1,1-trihalogeno-2-nitroethane (II) in high yield from the 1,1-dihalogenoethylene.

The completion of the reaction can be detected by the stop of an exothermic reaction, or the conventional analysis with an instrument such as gas chromatography, NMR, etc. The object compound (II) can be isolated by the conventional methods such as liquid separation, extraction and evaporation.

Examples of 1,1,1-trihalogeno-2-nitroethanes (II) thus obtained are 1,1,1-trichloro-2-nitroethane, 1-bromo-1,1-dichloro-2-nitroethane, 1,1-dibromo-1-chloro-2-nitroethane, 1-chloro-1,1-diiodo-2-nitroethane, 1,1-dichloro-1-fluoro-2-nitroethane, 1-chloro-1,1-difluoro-2-nitroethane, 1,1-dibromo-1-iodo-2-nitroethane, 1-bromo-1,1-diiodo-2-nitroethane, 1,1-dibromo-1-fluoro-2-nitroethane, 1-bromo-1,1-difluoro-2-nitroethane and 1,1,1-tribromo-2-nitroethane, among which especially 1,1,1-trichloro-2-nitroethane is industrially useful.

The 1,1,1-trihalogeno-2-nitroethane (II) is reacted with an amino compound of the formula (III):

wherein $R^1$, A and n have the same meanings as defined above, or its salt and an amino compound of the formula (IV):

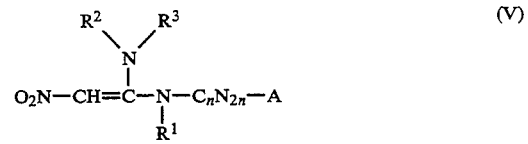

wherein $R^2$ and $R^3$ have the same meanings as defined above, or its salt to provide an α-unsaturated amine of the formula (V):

$$\begin{array}{c} R^2 \diagdown \diagup R^3 \\ N \\ | \\ O_2N-CH=C-N-C_nN_{2n}-A \\ | \\ R^1 \end{array} \quad (V)$$

wherein $R^1$, $R^2$, $R^3$, A and n have the same meanings as defined above or its salt.

The reaction is preferably conducted in the presence of a base, in order to avoid a consumption of the amino compound by a hydrogen halide which is produced as by-product of this reaction. Although there is no limitation of the order of addition of the two amino compounds (III) and (IV), it is preferable to conduct at first the reaction of a secondary amine in case of the combination of primary and secondary amines. Accordingly, it is possible to react the compound (II) with the compound (III), subsequently with the compound (IV), and alternatively to react the compound (II) with the compound (IV) followed by reacting with the compound (III).

Suitable examples of the bases to be employed in the reaction are organic bases such as triethylamine, tri-n-propylamine, pyridine, collidine, quinoline, dimethylaniline, methyldicyclohexylamine, 1,5-diazabicyclo[4.3.0]-non-5-ene, 1,4-diazabicyclo[2.2.2]-octane, 1,8-diazabicyclo[5.4.0]-7-undecene and 3,4-dihydro-2H-pyrido[1,2-a]-pyrimidin-2-one; inorganic bases such as sodium hydrogen carbonate, potassium hydrogen carbonate, sodium carbonate, potassium carbonate, sodium hydroxide, potassium hydroxide and calcium hydroxide; salts of carboxylic acids such as sodium acetate and potassium acetate. It is also possible to use as the base the amino compounds themselves which are used as the raw materials. The base is preferably used in 3 or more equivalents, to the compound (II), and there is no particular limitation in the timing of addition thereof as far as it does not impede the reacion.

The reaction is usually carried out in a solvent which does not impede the reaction. Suitable examples of the solvents are water; aliphatic hydrocarbons such as hexane, petroleum ether, ligroin and cyclohexane; aromatic hydrocarbons such as benzene, toluene, xylene and chlorobenzene; alcohols such as methanol, ethanol, n-propanol, isopropanol, n-butanol and tert-butanol; halogenated hydrocarbons such as chloroform, dichloromethane, carbon tetrachloride and 1,2-dichloroethane, ethers such as diethyl ether, diisopropyl ether, dioxane and tetrahydrofuran; ketones such as acetone and methyl ethyl ketone; nitriles such as acetonitrile and propionitrile; amides such as dimethylformamide and dimethylacetamide; esters such as methyl acetate, ethyl acetate and butyl acetate, and sulfoxides such as dimethyl sulfoxide.

The reaction temperature can be selected from the range of −80° C. or higher, but is generally −40° C. or higher, preferably −40° C. to 120° C., more preferably −20° C. to 50° C. The reaction will be completed within a relatively short time of 5 minutes to 5 hours. The object compound (V) after completion of the reaction can be isolated by the conventional methods such as filtration, concentration, extraction and column chromatography.

Also, the α-unsaturated amine (V) or its salt can be obtained by treating a 1,1,1-trihalogeno-2-nitroethane (II) with a base to obtain a 1,1-dihalogeno-2-nitroethylene (VI) and then reacting the compound (VI) with or without isolation with the amino compounds (III) and (IV) or salts thereof.

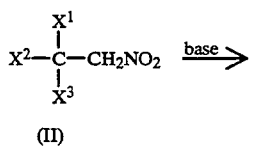

(II)

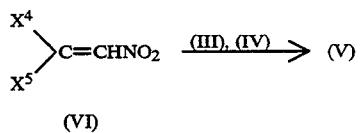

(VI)

The first reaction for obtaining the compound (VI) from the compound (II) and the base can be conducted with or without solvent. Suitable examples of the solvents to be employed are water; aliphatic hydrocarbons such as hexane, petroleum ether, ligroin and cyclohexane; aromatic hydrocarbons such as benzene, toluene, xylene and chlorobenzene; alcohols such as methanol, ethanol, n-propanol, isopropanol, n-butanol and tert-butanol; halogenated hydrocarbons such as chloroform, dichloromethane, carbon tetrachloride and 1,2-dichloroethane; ethers such as diethyl ether, diisopropyl ether, dioxane and tetrahydrofuran; ketones such as acetone and methyl ethyl ketone; nitriles such as acetonitrile and propionitrile; amides such as dimethylformamide and dimethylacetamide; esters such as methyl acetate, ethyl acetate and butyl acetate; and sulfoxides such as dimethyl sulfoxide.

Examples of the bases to be employed in the reaction are organic bases such as triethylamine, tri-n-propylamine, pyridine, collidine, quinoline, dimethylaniline, methyldicyclohexylamine, 1,5-diazabicyclo[4.3.0]-non-5-ene, 1,4-diazabicyclo[2.2.2]octane, 1,8-diazabicyclo[5.4.0]-7-undecene and 3,4-dihydro-2H-pyrido[1.2-a]pyrimidin-2-one; inorganic bases such as sodium hydrogen carbonate, potassium hydrogen carbonate, sodium carbonate, potassium carbonate, sodium hydroxide, potassium hydroxide and calcium hydroxide; salts of carboxylic acid salts such as sodium acetate and potassium acetate. Such bases are used in 1 to 5 equivalents, preferably 1 to 2 equivalents, to the compound (II). The reaction temperature can be selected in the range of −80° C. or higher, but is generally −40° C. or higher, preferably −40° C. to 120° C., more preferably −20° C. to 50° C.

The completion of the reaction can be detected, e.g. by gas chromatography, NMR, etc. The reaction will be completed within a relatively short time such as 15 minutes to 5 hours. For the isolation of the resulting product (VI), the conventional method such as extraction, filtration, concentration or evaporation is suitably utilized.

In the second reaction for obtaining the compound (V) from the compound (VI), the order of the reaction of two kinds of the amino compounds (III) and (IV) can be freely selected and, in case of the combination of a primary amine and a secondary amine, it is preferable to allow to firstly react the secondary amine. Any one of the compounds (III) and (IV) can be firstly used to react.

The reaction is preferably conducted in a solvent, to which those exemplified in the above mentioned first reaction are applicable. The reaction is preferably conducted in the presence of such base, to which those mentioned in the above mentioned first reaction are applicable. The base is used in 2 to 5 equivalents, preferably 2 to 3 equivalents, to the compound (VI). As occasion demands, it is also possible to use as such base the amino compound itself which is employed as the raw material. The reaction temperature can be chosen from the range of −80° C. or higher, preferably −40° C. to 120° C. but is generally −40° C. or higher, especially −20° C. to 50° C. The reaction time is relatively short and is 5 minutes to 5 hours.

The isolation of the resulting compound (V) after completion of the reaction can be carried out by the conventional method such as filtration, concentration, extraction and column chromatography.

In the above reactions, it is especially preferable to use secondary amines or salts thereof as either one or both of two kinds of the amino compounds (III) and (IV).

Examples of salts of the amino compounds (III) and (IV) are the salts with an inorganic acid such as hydrochloric acid, sulfuric acid or nitric acid; an organic acid such as benzenesulfonic acid; and a base such as sodium, potassium or lithium (e.g., $C_{1-4}alkyl\text{-}N\text{-}(Na)C_nH_{2n}\text{-}A$).

The amino compounds (III) and (IV) can be easily produced by the known methods, as described, e.g. in Organic Functional Group Preparations, Academic Press Vol 1, Chapter 13 (1968) and Vol 3, Chapter 10 (1972); survey of Organic Syntheses, Wiley-Interscience (1970), Chapter 8, or analogous methods thereto. Specific examples of the α-unsaturated-amines (V) as produced are shown in the Table 1.

TABLE 1

$$O_2N-CH=C(NR^2R^3)-N(R^1)-C_nH_{2n}-A$$

| Compound No. | $R^1$ | $R^2$ | $R^3$ | $C_nH_{2n}$ | A | Melting point |
|---|---|---|---|---|---|---|
| 1 | H | H | Me | $CH_2$ | 3-pyridyl | 159–160 |
| 2 | H | H | Et | $CH_2$ | 3-pyridyl | 161–162 |
| 3 | H | H | i-Pr | $CH_2$ | 3-pyridyl | 148–150 |
| 4 | H | H | n-Bu | $CH_2$ | 3-pyridyl | 110–112 |
| 5 | H | H | Allyl | $CH_2$ | 3-pyridyl | 114–115 |
| 6 | H | H | n-$C_5H_{13}$ | $CH_2$ | 3-pyridyl | 97–98 |
| 7 | H | H | Ph | $CH_2$ | 3-pyridyl | 217–218 |
| 8 | H | H | H | $CH_2$ | 3-pyridyl | 177–178 |
| 9 | H | H | n-PrS$(CH_2)_2$ | $CH_2$ | 3-pyridyl | 93–94 |
| 10 | H | H | $Me_2N(CH_2)_2$ | $CH_2$ | 3-pyridyl | 110–111 |
| 11 | H | H | HO$(CH_2)_2$ | $CH_2$ | 3-pyridyl | 161–163 |

TABLE 1-continued $$O_2N-CH=C\underset{R^1}{\overset{\underset{N}{\overset{R^2}{|}}\overset{R^3}{}}{|}}N-C_nH_{2n}-A$$

| Compound No. | $R^1$ | $R^2$ | $R^3$ | $C_nH_{2n}$ | A | Melting point |
|---|---|---|---|---|---|---|
| 12 | H | H | MeO(CH₂)₂ | CH₂ | 3-pyridyl | 108–109 |
| 13 | H | H | (MeO)₂CHCH₂ | CH₂ | 3-pyridyl | 96–98 |
| 14 | H | H | CF₃CH₂ | CH₂ | 3-pyridyl | 164–165 |
| 15 | H | H | Me₃SiCH₂ | CH₂ | 3-pyridyl | 156–157 |
| 16 | H | H | NH₂ | CH₂ | 3-pyridyl | 176–177 decomposition |
| 17 | H | Me | Me | CH₂ | 3-pyridyl | 68–70 |
| 18 | H | —(CH₂)₄— | | CH₂ | 3-pyridyl | 103–105 |
| 19 | H | —(CH₂)₂—N(Me)—(CH₂)₂— | | CH₂ | 3-pyridyl | oily form |
| 20 | H | —(CH₂)₂—O—(CH₂)₂— | | CH₂ | 3-pyridyl | 102–103 |
| 21 | H | —(CH₂)₅— | | CH₂ | 3-pyridyl | 106–108 |
| 22 | H | H | Me₂N | CH₂ | 3-pyridyl | 158–159 |

TABLE 1-continued
$$O_2N-CH=C(-NR^2R^3)-N(R^1)-C_nH_{2n}-A$$
| Compound No. | $R^1$ | $R^2$ | $R^3$ | $C_nH_{2n}$ | A | Melting point |
|---|---|---|---|---|---|---|
| 23 | Me | H | H | CH$_2$ | 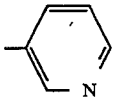 | 158–159 |
| 24 | Me | H | Me | CH$_2$ | 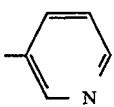 | 86–87 |
| 25 | H | H | Me | CH$_2$ | 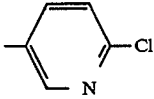 | 181–183 |
| 26 | Me | H | Me | CH$_2$ | 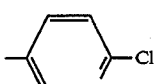 | 103–104 |
| 27 | Et | H | Me | CH$_2$ | 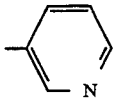 | oily form |
| 28 | (MeO)$_2$CHCH$_2$ | H | Me | CH$_2$ | 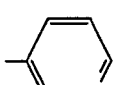 | oily form |
| 29 | Me | H | Et | CH$_2$ | 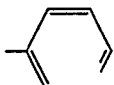 | oily form |
| 30 | Me | H | n-Bu | CH$_2$ | 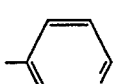 | oily form |
| 31 | MeO(CH$_2$)$_2$ | H | Me | CH$_2$ | 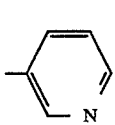 | oily form |
| 32 | Me | H | Allyl | CH$_2$ |  | oily form |
| 33 | Me | H | i-Pr | CH$_2$ |  | 119–121 |

TABLE 1-continued $$O_2N-CH=C(NR^2R^3)-N(R^1)-C_nH_{2n}-A$$

| Compound No. | R¹ | R² | R³ | $C_nH_{2n}$ | A | Melting point |
|---|---|---|---|---|---|---|
| 34 | Me | H | PhCH₂ | CH₂ | 3-pyridyl | oily form |
| 35 | Me | H | Me | CH₂ | quinolinyl | 145–147 |
| 36 | Me | H | Me | MeCH | 3-pyridyl | oily form |
| 37 | Me₂N | H | Me | CH₂ | 3-pyridyl | 109–110 |
| 38 | n-Pr | H | Me | CH₂ | 3-pyridyl | oily form |
| 39 | n-Bu | H | Me | CH₂ | 3-pyridyl | oily form |
| 40 | PhCH₂ | H | Me | CH₂ | 3-pyridyl | 118–119 |
| 41 | Me | H | H | CH₂ | 2-Cl-pyridyl | 206–207 |
| 42 | H | Me | Me | CH₂ | 2-Cl-pyridyl | 124–125 |
| 43 | H | H | Me | CH₂ | 2,6-diCl-pyridyl | 211–213 decomposition |

TABLE 1-continued $$O_2N-CH=C(NR^2R^3)-N(R^1)-C_nH_{2n}-A$$

| Compound No. | $R^1$ | $R^2$ | $R^3$ | $C_nH_{2n}$ | A | Melting point |
|---|---|---|---|---|---|---|
| 44 | Me | H | H | $CH_2$ | 2,5-dichloropyridin-3-yl | 214–215 decomposition |
| 45 | i-Pr | H | H | $CH_2$ | 6-chloropyridin-3-yl | powder |
| 46 | H | Me | Et | $CH_2$ | 6-chloropyridin-3-yl | 87–88 |
| 47 | H | H | $NH_2$ | $CH_2$ | 6-chloropyridin-3-yl | 188–190 decomposition |
| 48 | H | H | $Me_2N$ | $CH_2$ | 6-chloropyridin-3-yl | 170–172 |
| 49 | Me | H | Me | $CH_2CH_2$ | pyridin-3-yl | oily form |
| 50 | Me | Me | Me | $CH_2$ | pyridin-3-yl | 103–105 |
| 51 | Me | Me | (pyridin-3-yl)-$CH_2$ | $CH_2$ | pyridin-3-yl | oily form |
| 52 | Me | Me | Me | $CH_2$ | 6-chloropyridin-3-yl | 110–112 |
| 53 | Et | H | H | $CH_2$ | 6-chloropyridin-3-yl | 159–161 |
| 54 | Et | H | Me | $CH_2$ | 6-chloropyridin-3-yl | 83–84 |

TABLE 1-continued
$$O_2N-CH=C\underset{R^1}{\overset{\overset{R^2\phantom{xxx}R^3}{\underset{|}{N}}}{\underset{|}{N}}}-C_nH_{2n}-A$$
| Compound No. | R¹ | R² | R³ | $C_nH_{2n}$ | A | Melting point |
|---|---|---|---|---|---|---|
| 55 | Me | H | Me | $CH_2$ | 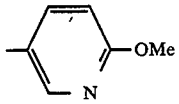 | 77–78 |
| 56 | Me | H | Me | $CH_2$ | 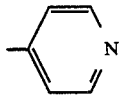 | 145–146 |
| 57 | Me | H | Me | $CH_2$ | 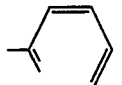 | 96–97 |
| 58 | MeO | H | Me | $CH_2$ | 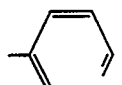 | 100–101 |
| 59 | Me | H | MeO(CH₂)₂ | $CH_2$ | 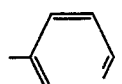 | 55–57 |
| 60 | Me | H | Me | $CH_2$ | 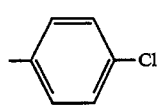 | 98–99 |
| 61 | H | H | H | $CH_2$ | 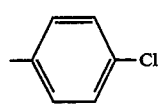 | 215–216 decomposition |
| 62 | H | H | Me | $CH_2$ | 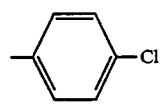 | 219–220 decomposition |
| 63 | H | Me | Me | $CH_2$ |  | 133–135 |
| 64 | Me | H | Me | $CH_2$ | 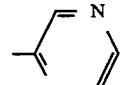 | 132–133 |
| 65 | Me | H | Me₂N | $CH_2$ | 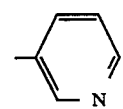 | 80–82 |

TABLE 1-continued
$$O_2N-CH=C\genfrac{}{}{0pt}{}{\overset{R^2\ \ R^3}{\underset{|}{N}}}{\underset{R^1}{|}}-\underset{R^1}{N}-C_nH_{2n}-A$$
| Compound No. | R¹ | R² | R³ | $C_nH_{2n}$ | A | Melting point |
|---|---|---|---|---|---|---|
| 66 | n-Pr | H | H | CH₂ | 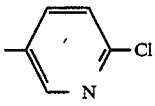 | 185–186 decomposition |
| 67 | n-Pr | H | Me | CH₂ | 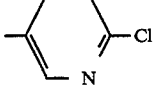 | 102–103 |
| 68 | i-Pr | H | Me | CH₂ | 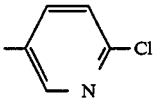 | 119–120 |
| 69 | Me | H | Me | — | 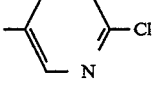 | 108–109 |
| 70 | Me | H | Me | — | 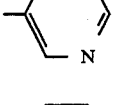 | 113–114 |
| 71 | Me | H | Et | CH₂ | 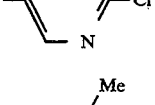 | 132–133 |
| 72 | Me | H | Me | CH₂ | 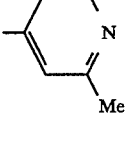 | 131–133 |
| 73 | Me | H | Me | CH₂ | 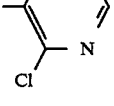 | 106–113 |
| 74 | Me | H | Me | — | 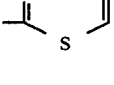 | 155–156 |
| 75 | Me | H | Me | — | 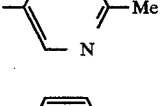 | 120–121 |
| 76 | Me | H | Et | — | 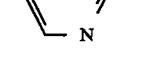 | 118–119 |

TABLE 1-continued $$O_2N-CH=C\underset{R^1}{\overset{\overset{R^2\ R^3}{N}}{\underset{|}{N}}}-C_nH_{2n}-A$$

| Compound No. | $R^1$ | $R^2$ | $R^3$ | $C_nH_{2n}$ | A | Melting point |
|---|---|---|---|---|---|---|
| 77 | Me | H | Me | $CH_2$ | 5-bromo-3-pyridyl | 116–117 |
| 78 | Me | H | Me | $CH_2$ | 2-(methylthio)-5-pyridyl | 131–132 |
| 79 | Me | H | Me | $CH_2$ | thiazol-5-yl | 155–156 |
| 80 | H | H | (6-chloro-3-pyridyl)$CH_2$ | $CH_2$ | 6-chloro-3-pyridyl | 238–240 decomposition |
| 81 | Et | H | Me | — | 6-chloro-3-pyridyl | 95–95 |
| 82 | n-Pr | H | Me | — | 6-chloro-3-pyridyl | 94–95 |
| 83 | n-Bu | H | Me | — | 6-chloro-3-pyridyl | 87–88 |
| 84 | Et | H | Et | — | 6-chloro-3-pyridyl | 105 |
| 85 | Me | H | Me | — | 4-(trifluoromethyl)-3-pyridyl | 114–115 |
| 86 | Me | H | n-Pr | — | 6-chloro-3-pyridyl | oily form |
| 87 | H | H | Me | — | 6-chloro-3-pyridyl | 185 decomposition |

TABLE 1-continued
$$O_2N-CH=C\overset{\overset{R^2}{\underset{|}{N}}\overset{R^3}{}}{\underset{\underset{R^1}{|}}{N}}-C_nH_{2n}-A$$
| Compound No. | $R^1$ | $R^2$ | $R^3$ | $C_nH_{2n}$ | A | Melting point |
|---|---|---|---|---|---|---|
| 88 | Me | H | Me | CH$_2$ | 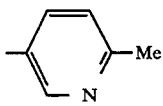 | 102–103 |
| 89 | Me | H | Me | CH$_2$ | 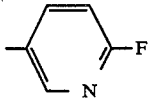 | 100–100.5 |
| 90 | Et | H | Me | CH$_2$ | 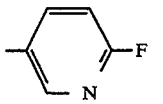 | oily form |
| 91 | Me | H | Me | CH$_2$ | 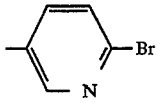 | 130–131 |
| 92 | Et | H | Me | CH$_2$ | 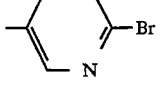 | 79–80 |
| 93 | Me | H | Me | CH$_2$ | 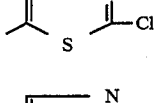 | 131–133 |
| 94 | Et | H | Me | CH$_2$ | 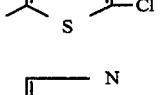 | 110–112 |
| 95 | H | Me | Me | CH$_2$ | 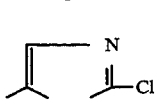 | 101–102 |
| 96 | H | H | 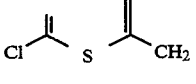 | CH$_2$ | 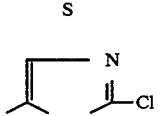 | 211 decomposition |
| 97 | H | H | Me | CH$_2$ | 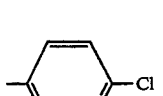 | 181 decomposition |
| 98 | H | Me | Me | — | 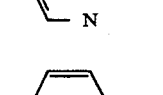 | 122–123 |
| 99 | Me | H | Me | — | 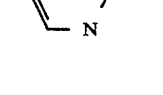 | 131–132 |

TABLE 1-continued $$O_2N-CH=C(\overset{R^2}{\underset{}{\overset{|}{N}}}\overset{R^3}{)}-\underset{R^1}{\overset{|}{N}}-C_nH_{2n}-A$$

| Compound No. | $R^1$ | $R^2$ | $R^3$ | $C_nH_{2n}$ | A | Melting point |
|---|---|---|---|---|---|---|
| 100 | H | H | Me | $CH_2$ | 2-Br-pyridin-5-yl | 184–186 decomposition |
| 101 | H | Me | Me | $CH_2$ | 2-Br-pyridin-5-yl | 158–159 |
| 102 | Me | H | H | $CH_2$ | 2-Br-pyridin-5-yl | 206–207 |
| 103 | $CF_3CH_2$ | H | Me | $CH_2$ | 2-Cl-pyridin-5-yl | 110–111 |
| 104 | H | H | Me | $CH_2$ | 2-Cl-5-Me-4-Cl-thiazole | 182–184 decomposition |
| 105 | H | H | Me | $CH_2$ | 2-Br-thiazol-5-yl | 167–169 decomposition |
| 106 | H | Me | Me | $CH_2$ | 2-Br-thiazol-5-yl | 125 decomposition |
| 107 | Et | Me | Me | $CH_2$ | 2-Cl-pyridin-5-yl | oily form |
| 108 | $CH_2FCH_2$ | H | Me | $CH_2$ | 2-Cl-pyridin-5-yl | 78–79 |
| 109 | $CH_2FCH_2$ | Me | Me | $CH_2$ | 2-Cl-pyridin-5-yl | 90–91 |
| 110 | $CH_2FCH_2$ | H | Me | $CH_2$ | 2-Br-pyridin-5-yl | — |
| 111 | $CH_2FCH_2$ | Me | Me | $CH_2$ | 2-Br-pyridin-5-yl | — |

TABLE 1-continued $$O_2N-CH=\underset{\underset{R^1}{|}}{\overset{\overset{R^2}{|}\phantom{xx}\overset{R^3}{|}}{\overset{N}{C}}}-N-C_nH_{2n}-A$$

| Compound No. | $R^1$ | $R^2$ | $R^3$ | $C_nH_{2n}$ | A | Melting point |
|---|---|---|---|---|---|---|
| 112 | $CH_2FCH_2$ | H | Me | $CH_2$ | 2-chloro-thiazol-5-yl | |
| 113 | Me | Me | Me | $CH_2$ | 2-chloro-thiazol-5-yl | |
| 114 | Et | Me | Me | $CH_2$ | 2-chloro-thiazol-5-yl | |
| 115 | Me | H | Me | $CH_2$ | 2-bromo-thiazol-5-yl | |
| 116 | Et | H | Me | $CH_2$ | 2-bromo-thiazol-5-yl | |
| 117 | $CH_2FCH_2$ | Me | Me | $CH_2$ | 2-chloro-thiazol-5-yl | |
| 118 | Me | Me | Me | $CH_2$ | 2-bromo-thiazol-5-yl | |
| 119 | Et | Me | Me | $CH_2$ | 2-bromo-thiazol-5-yl | |
| 120 | $ClCH_2$ | H | Me | $CH_2$ | 2-chloro-pyridin-5-yl | |
| 121 | $ClCH_2$ | H | Me | $CH_2$ | 2-bromo-pyridin-5-yl | |
| 122 | $ClCH_2$ | H | Me | $CH_2$ | 2-chloro-thiazol-5-yl | |
| 123 | $CH_2FCH_2$ | H | Me | $CH_2$ | 2-bromo-thiazol-5-yl | |
| 124 | $CH_2FCH_2$ | Me | Me | $CH_2$ | 2-bromo-thiazol-5-yl | |

TABLE 1-continued $$O_2N-CH=C(\overset{R^2\diagdown N\diagup R^3}{\underset{R^1}{|}})-N-C_nH_{2n}-A$$

| Compound No. | $R^1$ | $R^2$ | $R^3$ | $C_nH_{2n}$ | A | Melting point |
|---|---|---|---|---|---|---|
| 125 | $CF_3CH_2$ | H | Me | $CH_2$ | 2-chloro-thiazol-5-yl | |
| 126 | $CF_3CH_2$ | Me | Me | $CH_2$ | 6-bromo-pyridin-3-yl | |
| 127 | Me | Me | Me | $CH_2$ | 6-bromo-pyridin-3-yl | |
| 128 | Et | Me | Me | $CH_2$ | 6-bromo-pyridin-3-yl | |
| 129 | H | H | Me | $CH_2$ | 6-fluoro-pyridin-3-yl | |
| 130 | H | Me | Me | $CH_2$ | 6-fluoro-pyridin-3-yl | |
| 131 | Me | Me | Me | $CH_2$ | 6-fluoro-pyridin-3-yl | |
| 132 | Et | Me | Me | $CH_2$ | 6-fluoro-pyridin-3-yl | |
| 133 | Et | $-(CH_2)_4-$ | | $CH_2$ | 6-chloro-pyridin-3-yl | 110–111 |
| 134 | Et | Et | Et | $CH_2$ | 6-chloro-pyridin-3-yl | 105–106 |
| 135 | Et | H | i-Pr | $CH_2$ | 6-chloro-pyridin-3-yl | 126–127.5 |

TABLE 1-continued
$$O_2N-CH=C\underset{\underset{R^1}{|}}{\overset{\overset{R^2}{|}\underset{N}{\diagup}\overset{R^3}{\diagdown}}{N}}-C_nH_{2n}-A$$
| Compound No. | $R^1$ | $R^2$ | $R^3$ | $C_nH_{2n}$ | A | Melting point |
|---|---|---|---|---|---|---|
| 136 | Et | H | t-Bu | $CH_2$ | 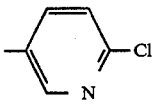 | 151–152 |
| 137 | $CH_2FCH_2$ | H | H | $CH_2$ | 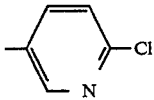 | 152–153 |
| 138 | Et | H | Et | $CH_2$ | 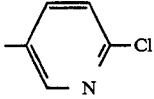 | 123–125 |
| 139 | Et | H |  | $CH_2$ | 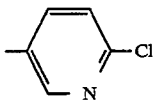 | 74–75 |
| 140 | Et | MeO | Me | $CH_2$ | 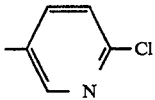 | oily form |
| 141 | Et | MeO | H | $CH_2$ | 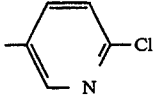 | oily form |
| 142 | Et | Me | Et | $CH_2$ | 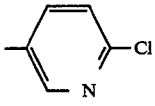 | oily form |
| 143 | Et | H | $Me_2N$ | $CH_2$ | 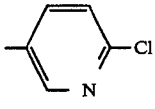 | oily form |
| 144 |  | H | Me | $CH_2$ | 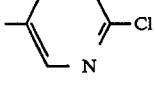 | 115–116 |
| 145 |  | H | H | $CH_2$ | 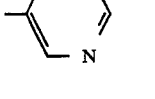 | oily form |
| 146 |  | H | H | $CH_2$ | 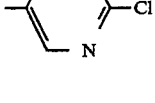 | 128–129 |

TABLE 1-continued $$O_2N-CH=\underset{\underset{R^1}{|}}{\overset{\overset{R^2\diagdown\diagup R^3}{N}}{C}}-N-C_nH_{2n}-A$$

| Compound No. | $R^1$ | $R^2$ | $R^3$ | $C_nH_{2n}$ | A | Melting point |
|---|---|---|---|---|---|---|
| 147 | cyclopropyl | Me | Me | $CH_2$ | pyridyl | oily form |
| 148 | cyclopropyl | Me | Me | $CH_2$ | 2-chloropyridyl | 73–75 |
| 149 | Et | H | Me | $CH_2$ | 2,3-dichloropyridyl | 108–109 |

*1 exists as $O_2N-CH_2-\underset{\underset{Et}{|}}{\overset{\overset{N\diagup OMe}{\|}}{C}}-N-CH_2-$(2-chloro-5-pyridyl)

*2 exists as $O_2N-CH_2-\underset{\underset{Et}{|}}{\overset{\overset{N\diagup NMe_2}{\|}}{C}}-N-CH_2-$(2-chloro-5-pyridyl)

In the above table, Me, Et, n-Pr, i-Pr and n-Bu represent $CH_3-$, $CH_3CH_2-$, $CH_3CH_2CH_2-$, $$\underset{CH_3}{\overset{CH_3}{\diagdown}}CH-\text{ and }CH_3CH_2CH_2CH_2-,\text{ respectively.}$$

When the compound (V) is obtained in the free form, it may be converted into its salt form by the conventional method and, on the contrary, the salt when obtained may be converted into the corresponding free form by the conventional method. That is, when the compound (V) has a basic group or moiety in the parts of $R^1$, $R^3$ and A, it may form the acid addition salt, e.g., the hydrochloride, hydrobromide, hydroiodide, nitrate, sulfate, phosphate, acetate, benzoate, maleate, fumalate, succinate, tartarate, citrate, oxalate, glyoxylate, aspartate, methanesulfonate, methanedisulfonate, 1,2-ethanedisulfonate or benzenesulfonate. Also, the compound (V) may form an inner salt which is also included in this invention.

The compounds (V) can exist as stereoisomers and tautomers, and such isomers and mixtures thereof are also included in this invention.

The compounds (V) or their salts are effective in preventing sanitary or horticultural insect pests and animal and plant parasites and can exert potent insecticidal activities when they are directly contacted with insects, e.g., by applying to their living animals or plants. An interesting characteristic property of the compounds (V) or their salts is found in that potent insecticidal activities can be achieved by once absorbing the compounds in plants through their root, leaves or stem which are then sucked or bitten by insects or contacted with insects. Such property is Advantageous for preventing suctorial type or mandible type insecticides. Moreover, the compounds (V) and their salts possess safe and advantageous properties as agents for preventing agricultural injurious insects, such as no substantial damage on plants and less toxicity against fishes.

Specifically, the preparations containing the compounds (V) or their salts are especially effective in preventing Hemiptera injurious insects such as *Eurydema rugosum, Scotinophara lurida, Riptortus clavatus, Stephanitis nashi, Laodelphax striatellus, Nalaparvate lugens, Nephotettix cincticeps, Unaspis yanonensis, Aphis glycines, Lipaphis erysimi, Brevicoryne brassicae, Aphis gissypii, Sogattela furcifera, Nezara viridula, Trialeurodes vaporariorum, Myzus persicae, Pseudococcus comstocki, Aphis promi Nezara spp, Cimex lectularius* and *Psylla spp;* Lepidoptera injurious insects such as *Spodoptera litura, Plutella xylostella, Pieris rapae crucivora, Chilo suppressalis, Autographa nigrisigna, Helicoverpa assulta, Pseudaletia separata, Mamestra brassicae, Adoxophyes orana fasciata, Notarcha derogata, Cnaphalocrocis medinalis* and *Phthorimaea operculella;* Coleoptera injurious insects such as *Epilachna vigintioctopunctata, Aulacophora, femoralis, Phyllotreta striotata, Oulema oryzae* and *Echinocnemus squameus;* Diptera injurious insects such as *Musca domestica, Culex pipiens pallens, Tabanus trigonus, Delia antiqua* and *Delia platura;* Orthoptera injurious insects such as *Locusta migratoria* and *Gryllotalpa*

*africana;* Dictyoptera injurious insects such as *Blattella germanica* and *Periplaneta fuliginosa;* Tetranychidaes such as *Tetranychus urticae, Panonychus citri, Tetranychus kanzawai, Tetranychus cinnabarinus, Panonychus ulmi* and *Aculops pelekassi;* and Nematodes such as *Aphelenchoides besseyi.*

The compounds (V) or their salts can be used as insecticides or miticides in any application form suited for general agricultural chemicals. That is, one, two, or more than two kinds of the compounds (V) or their salts are used in the form of preparation such as emulsifiable concentrates, oil solutions, wettable powders, dusts, granules, tablets, sprays or ointments, according to the purpose of use, by dissolving or dispersing them in suitable liquid carriers, or mixing them with or absorbing them on suitable solid carriers. These preparations may contain, if necessary, emulsifying agent, suspending agent, spreading agent, penetrating agent, wetting agent, thickening agent or stabilizer, and can be prepared by any conventional method known per se.

The rate of the compound (V) or a salt thereof contained in an insecticidal preparation is suitably about 10 to 90% by weight in the case of emulsifiable concentrates or wettable powders, about 0.1 to 10% by weight in the case of oil solution or dust and about 1 to 20% by weight in the case of granules. However, such concentration may be changed properly, depending on the purpose of use. Emulsifiable concentrates, wettable powders or the like are suitably diluted or extended (for example, to 10 to 100000 times) with water or the like, on the occasion or use, and then scattered.

Suitable examples of the liquid carriers (solvents) include solvents such as water, alcohols (for example, methanol, ethanol, n-propanol, isopropanol or ethylene glycol), ketones (for example, acetone or methyl ethyl ketone), ethers (for example, dioxane, tetrahydrofuran, ethylene glycol monomethyl ether, di-ethylene glycol monomethyl ether or propylene glycol monomethyl ether), aliphatic hydrocarbons (for example, kerosine, kerosene oil, fuel oil or machine oil), aromatic hydrocarbons (for example, benzene, toluene, xylene, solvent naphtha or methylnaphthalene), halogenated hydrocarbons (for example, dichloromethane, chloroform or carbon tetrachloride), acid amides (for example, dimethylformamid or dimethyl acetamide), esters (for example, ethyl acetate, butyl acetate or fatty acid glycerol ester )or nitriles (for example, acetonitrile or propionitrile). These solvents are used individually or as a suitable mixture of two, or more, of them.

Suitable examples of the solid carriers (diluents or dust carrier) include vegetable powder (for example, soybean meal, tobacco meal, wheat flour or wood flour), mineral powders (for example, clays such as kaolin, bentonite, or acid clay, talcs such as talc powder or pyrophyllite powder), silicas (for example, diatomaceous earth or mica powder), aluminas, sulfur powder or active carbon. They are used individually or as a suitable mixture of two, or more, of them.

Also, suitable examples of bases for ointments include polyethylene glycol, pectin, polyalcohol esters of higher aliphatic acids (for example, glycerin mono-stearate), cellulose derivatives (for example, methyl cellulose), sodium alginate, bentonite, higher alcohols, polyalcohos (for example, glycerin), vaseline, white petrolatum, liquid paraffin, lard, various vegetable oils, lanolin, dehydrated lanolin, hard oil or resins. They are used individually, or as a suitable mixture of two, or more, of them or together with surface active agents mentioned below.

As surface active agents used as the emulsifying agent, spreading agent, penetrating agent or dispersing agent, nonionic or anionic surface active agents such as soaps; polyoxyethylene alkyl aryl ethers (e.g., Noigen® and E.A 142® from Dai-ichi Kogyo Seiyaku K.K., Japan, and Nonal® from Toho Chemical, Japan); alkyl sulfates (e.g., Emal 10® and Emal 40® from Kao K.K., Japan); alkyl sulfonates (e.g., Neogen® and Neogen T® from Dai-ichi Kogyo Seiyaku K.K. and Neopellex® from Kao K.K.); polyethylene glycol ethers (e.g., Nonipol 85®, Nonipol 100®, Nonipol 160® from Sanyo Kasei K.K., Japan); or polyhydric alcohol esters (e.g., Tween 20® and Tween 80® from Kao K.K.) are used, if necessary.

The compounds (V) or their salts can also be used, as occasion demands, in combination with or as an admixture with other insecticides (for example, pyrethroid insecticides, organophosphorus insecticides, carbamate insecticides or natural insecticides), acaricides, nematocides, herbicides, plant hormones, plant growth regulators, fungicides (for example, copper fungicides, organic chlorine fungicides, organic sulfur fungicides or phenol fungicides), synergistic agents, attractants, repellents, pigments and/or fertilizers.

The insecticidal or miticidal composition comprising the compound (V) or its salt of the present invention is an excellent agricultural product having fairly low toxicity and good safety. It can be used in a similar way to the conventional insecticidal or miticidal composition and can exert excellent effects in comparison with the conventional compositions. For example, the insecticidal or miticidal compositions of the present invention can be applied to the target insects, by treatment in nursery box, application for stem and leaf of crop, spraying for insects, application in water of a paddy field or soil treatment of a paddy field. The amount of application may broadly vary depending on the season, place and method of application, and so forth. However, the active ingredient (the compound (V) or its salt) is used in general, in an amount of 0.3 g to 3,000 g, preferably 50 g to 1,000 g per hectare. When the insecticidal composition of the present invention is in a wettable powder, it can be used by diluting it so as to be 0.1–1000 ppm, preferably 10–500 ppm as the final concentration of the active ingredient.

Activity

As will be clear from the following tests, the compounds (I) and salts thereof possess excellent insecticidal activities.

TEST EXAMPLE 1

(Effect against *Nilaparvata lugens*)

5 mg of each of test compounds (shown by Compound No. obtained in Example as stated hereinafter) was dissolved in 0.5 ml of acetone containing Tween 20® and diluted to a predetermined concentration (500 ppm) by addition of Dyne® (a spreader produced by Takeda Chemical Industries, Ltd. of Japan) diluted 3000 times with water. The solution at a rate of 10 ml/pot was sprayed on leaf and stem of rice seedlings at the second leaf stage raised in a nursery box. The treated rice seedlings were put into a test tube containing water at the bottom, to which 10 larvae at 3 instar of *Nilaparvata lugens* were released. After being sealed with an aluminum stopper, the test tube was kept in an incubator adjusted to 25° C. Death number was counted 7 days after release. The mortality rate was calculated by the following formula and shown in Table 2.

$$\text{Mortality (\%)} = \frac{\text{the number of dead insects}}{\text{the number of insects released}} \times 100$$

TABLE 2

| Compound No. | Mortality (%) |
|---|---|
| 1 | 100 |
| 2 | 100 |
| 5 | 100 |
| 10 | 100 |
| 12 | 100 |
| 15 | 100 |
| 16 | 100 |
| 17 | 100 |
| 18 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 33 | 100 |
| 34 | 100 |
| 36 | 100 |
| 37 | 100 |
| 38 | 100 |
| 39 | 100 |
| 40 | 100 |
| 41 | 100 |
| 42 | 100 |
| 43 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |
| 56 | 100 |
| 58 | 100 |
| 59 | 100 |
| 60 | 100 |
| 62 | 100 |
| 63 | 100 |
| 64 | 100 |
| 66 | 100 |
| 67 | 100 |
| 68 | 100 |
| 69 | 100 |
| 70 | 100 |
| 71 | 100 |
| 75 | 100 |
| 76 | 100 |
| 77 | 100 |
| 79 | 100 |
| 80 | 100 |
| 81 | 100 |
| 82 | 100 |
| 83 | 100 |
| 84 | 100 |
| 86 | 100 |
| 87 | 100 |
| 88 | 100 |
| 89 | 100 |
| 90 | 100 |
| 91 | 100 |
| 92 | 100 |
| 93 | 100 |
| 94 | 100 |
| 95 | 100 |
| 96 | 100 |
| 97 | 100 |
| 98 | 100 |
| 99 | 100 |
| 100 | 100 |
| 101 | 100 |
| 102 | 100 |
| 103 | 100 |
| 105 | 100 |
| 106 | 100 |
| 107 | 100 |
| 108 | 100 |
| 109 | 100 |
| 133 | 100 |
| 134 | 100 |
| 135 | 100 |
| 137 | 100 |
| 138 | 100 |
| 139 | 100 |
| 140 | 100 |
| 141 | 100 |
| 142 | 100 |
| 144 | 100 |
| 145 | 100 |
| 146 | 100 |
| 147 | 100 |
| 148 | 100 |
| 149 | 100 |

Table 1 clearly reveals that the compounds (V) or salts thereof have an excellent insecticidal effect on *Nilaparvate lugens*.

REFERENCE EXAMPLE 1,1-Dichloroethylene 4.85 g (0.05 mol) was dropwise added to 5.40 g (0.06 mol) of 70% nitric acid at 23°–27° C. with stirring. After stirring for an hour at 23°–25° C., the lower layer of the reaction mixture was collected, added with 10 ml of ethyl ether and washed with 10 ml of water. Then, the mixture was dried over magnesium sulfate and concentrated to obtain 6.21 g of a crude product, which was found to contain 33% of 1,1,1-trichloro-2-nitroethane and 8% of 1,1,1,2-tetrachloroethane by NMR measurement.

EXAMPLE 1

To the mixture of 5.6 g of 36% hydrochloric acid (0.055 mol) and 4.5 g (0.05 mol) of 70% nitric acid (d 1.42) were dropwise added 4.85 g (0.05 mol) of 1,1-dichloroethylene in 15 minutes at 23°–26° C. The reaction mixture was stirred at the same temperature for an hour and then extracted with chloroform. The chloroform layer was washed with water, dried over magnesium sulfate and concentrated to yield 6.4 g (71.7%) of 1,1,1-trichloro-2-nitroethane. bp. 82.5°–84° C./24 mmHg

EXAMPLE 2

7.6 g (0.075 mol) of 36% hydrochloric acid, 4.5 g (0.05 mol) of 70% nitric acid and 4.85 g (0.05 mol) of 1,1-dichloroethylene were treated in the same way as in Example 1 to obtain 1,1,1-trichloro-2-nitroethane. Yield: 6.2 g (69.5%).

EXAMPLE 3

7.6 g (0.075 mol), of 36% hydrochloric acid, 6.8 g (0.075 mol) of 70% nitric acid and 4.85 g (0.05 mol) of 1,1-dichloroethylene were treated in the same way as in Example 1 to obtain 1,1,1-trichloro-2-nitroethane. Yield: 5.4 g (60.5%).

EXAMPLE 4

To the mixture of 4.5 g (0.05 mol) of 70% nitric acid and 4.85 g (0.05 mol) of 1,1-dichloroethylene were dropwise added, 5.6 g (0.055 mol) of 36% hydrochloric acid in 15 minutes at 23°-26° C. The reaction mixture was stirred at the same temperature and then extracted with chloroform, the chloroform layer was dried over magnesium sulfate and concentrated to obtain 1,1,1-trichloro-2-nitroethane. Yield: 5.7 g (63.9%).

EXAMPLE 5

To the mixture of 5.6 g (0.055 mol) of 36% hydrochloric acid and 4.85 g (0.05 mol) of 1,1-dichloroethylene were dropwise added, 4.5 g (0.05 mol) of 70% nitric acid in 15 minutes at 23°-26° C. with stirring. The reaction mixture was stirred for an hour at the same temperature and then extracted with chloroform. The chloroform layer was washed with water, dried over magnesium sulfate and concentrated to obtain 1,1,1-trichloro-2-nitroethane. Yield: 5.8 g (65.0%).

EXAMPLE 6

5.6 g (0.055 mol) of 36% hydrochloric acid and 3.35 g (0.05 mol) of 94% fuming nitric acid (d. 1.50) were mixed, to which 4.85 g (0.05 mol) of 1,1-dichloro ethylene was dropwise added with in 15 minutes at 23°-26° C. with stirring. The reaction mixture was stirred for an hour at the same temperature and extracted with chloroform. The chloroform layer was washed with water, dried over magnesium sulfate and concentrated to obtain 1,1,1-trichloro-2-nitroethane. Yield: 6.02 g (67.5%).

EXAMPLE 7

To the mixture of 3.21 g (0.055 mol) of sodium chloride and 4.85 g (0.05 mol) of 1,1-dichloroethylene were dropwise added 9.45 g (0,105 mol) of 70% nitric acid in 15 minutes at 23°-26° C. with stirring. The reaction mixture was stirred at the same temperature for 2 hours and then extracted with ethyl acetate. The extract was washed with water, dried over magnesium sulfate and concentrated to obtain 1,1,1-trichloro-2-nitroethane. Yield: 4.3 g (48.2%).

EXAMPLE 8

A solution of 9.7 g (0.1 mol) of 1,1-dichloroethylene in 10 ml of toluene was dropwise added to the mixture of 11.2 g (0.11 mol) of 36% hydrochloric acid and 9.0 g (0.1 mol) of 70% nitric acid at 23°-26° C. with stirring. This reaction mixture was stirred for 15 hours at the same temperature. The separated toluene layer was washed with water, dried over magnesium sulfate and concentrated to obtain 1,1,1-trichloro-2-nitroethane. Yield: 12.4 g (69.5%).

EXAMPLE 9

To a mixture of 9.5 g (0.055 mol) of 47% hydrobromic acid and 4.5 g (0.05 mol) of 70% nitric acid were added 4.85 g (0.05 mol) of 1,1-dichloroethylene in 15 minutes at 23°-26° C. with stirring. The reaction mixture was stirred for 2 hours at the same temperature and then extracted with chloroform. The extract was washed with water, dried over magnesium sulfate and concentrated to obtain 8.5 g (76.3%) of 1-bromo-1,1-dichloro-2-nitroethane. bp. 92°-93° C./25 mm Hg NMR(CDCl$_3$)δ ppm=5.33(s)

EXAMPLE 10

To a solution of 2.83 g (0.0158 mol) of 1,1,1-trichloro-2-nitroethane in 40 ml of acetonitrile were added 2.86 g (0.0207 mol) of K$_2$CO$_3$, followed by stirring for 30 minutes at room temperature (15°-20° C.). The reaction mixture was cooled to 5°-7° C., to which a solution of 2.72 g (0.0158 mol) of N-(6-chloro-3-pyridyl)methyl-N-ethylamine in 4 ml of acetonitrile was dropwise added and stirred for 45 minutes. To the reaction mixture were added 2.2 g (0.016 mol) of K$_2$CO$_3$ and subsequently 1.6 g (0.0206 mol) of methylamine (40% methanolic solution) at 18°-20° C., followed by stirring for an hour at the same temperature. The reaction mixture was filtered, and the filtrate was concentrated. The residue was purified by a silica gel column chromatography (chloroform/ethanol=85/15) to afford 2.63 g (62.7%) of 1-[N-6-chloro-3-pyridyl)-methyl-N-ethyl]amino-1-methylamino-2-nitroethylene as pale yellowish crystals. mp. 83°-84° C.

EXAMPLE 11

A solution of 6.2 g of 1,1,1-trichloro-2-nitroethane in 30 ml of chloroform was added to 80 ml of 2% sodium hydroxide aqueous solution cooled at 0° C. under stirring. Immediately, the aqueous layer was separated and extracted with chloroform. The combined chloroform layers were dried over magnesium sulfate and concentrated to yield 4.0 g of 1,1-dichloro-2-nitroethylene (yield: 81.1%). NMR(CDCl$_3$)δ ppm=7.65(s)

EXAMPLE 12

A solution of 2.4 g (0.014 mol) of N-(6-chloro-3-pyridyl)methyl-N-ethylamine, 1.4 g (0.014 mol) of triethylamine in 5 ml of acetonitrile was dropwise added to a solution of 2.0 g (0.014 mol) of 1,1-dichloro-2-nitroethylene in 35 ml of acetonitrile at 3°-5° C. with stirring. After stirring for 30 minutes, 4.4 g (0.057 mol) of methylamine (40% methanol solution) were added to the reaction mixture and stirred for 30 minutes. The reaction mixture was filtered, and the filtrate was concentrated and purified by a silica gel column chromatography (chloroform/ethanol=7/1) to afford 2.9 g (76.5%) of 1-[N-(6-chloro-3-pyridyl)methyl-N-ethyl-]amino-1-methylamino-2-nitroethylene as pale yellowish crystals. This substance was identified as the same substance with that obtained in Example 10.

EXAMPLE 13

To a mixture of 65.83 g (0.65 mol) of 36% hydrochloric acid and 58.51 g (0.65 mol) of 70% nitric acid was dropwise added 48.96 g (0.5 mol) of 1,1-dichloroethylene (purity: 99%) at 17°-24.5° C., taking an hour and 16 minutes with stirring. After stirring for about 1.5 hours at 20°-22° C., the lower layer of the reaction mixture was collected and washed with 45 ml of water. The mixture to which 150 ml of ethyl ether were added was dried over magnesium sulfate and concentrated to obtain 69.81 g (78.3%) of 1,1,1-trichloro-2-nitroethane. The product was distilled under reduced pressure to obtain colorless oil of bp. 82.5°-84° C./24mmHg. NMR(CDCl$_3$)δ ppm: 5.26(s)

EXAMPLE 14

The method of Example 13 was repeated by using equivalent amounts of 36% hydrochloric acid and 70% nitric acid but varying their molar ratios to 1,1- dichloroethylene, to obtain 1,1,1-trichloro-2-nitroethane. The results are shown in Table 3.

TABLE 3

| Molar ratio of 36% HCl and 70% HNO$_3$ | Yield of 1,1,1-trichloro-2-nitroethane (%) |
|---|---|
| 1.0 & 1.0 | 63.0 |
| 1.1 & 1.1 | 70.5 |
| 1.2 & 1.2 | 76.0 |
| 1.3 & 1.3 | 78.3 |
| 1.4 & 1.4 | 76.9 |
| 1.5 & 1.5 | 76.4 |

EXAMPLE 15

The method of Example 13 was repeated by using 35% hydrochloric acid and 67.5% nitric acid but varying their molar ratios to 1,1-dichloroethylene, to obtain 1,1,1-trichloro-2-nitroethane. The results are shown in Table 4.

TABLE 4

| Molar ratio of 35% HCl | Molar ratio of 67.5% HNO$_3$ | | | | | |
|---|---|---|---|---|---|---|
| | 1.0 | 1.1 | 1.2 | 1.3 | 1.5 | 2.0 |
| 1.0 | 59.9* | 63.6 | 66.4 | 71.8 | — | — |
| 1.1 | 59.4 | 67.5 | 70.6 | 74.2 | — | — |
| 1.2 | 65.3 | 69.1 | 73.8 | 77.0 | — | — |
| 1.3 | 68.1 | 73.4 | 76.1 | 77.7 | — | — |
| 1.5 | — | — | — | — | 75.7 | — |
| 2.0 | — | — | — | — | — | 66.4 |

*Yield (%) of 1,1,1-trichloro-2-nitroethane

As is clear from Tables 3 and 4, it is found that the good yields are achieved in use of 1.2–1.5 moles of each of hydrochloric acid and nitric acid, to one mole of the raw material while the use of 1.1 or less moles produces significantly lowered yield.

EXAMPLE 16

To a mixture of 4.25 g (0.05 mol) of sodium nitrate and 4.85 g (0.05 mol) of 1,1-dichloroethylene was dropwise added 10.64 g (0.105 mol) of 36% hydrochloric acid at 23°–26° C. in 30 minutes, with stirring. After stirring for 3 hours at the same temperature, the lower layer was collected and 30 ml of chloroform were added to it. Then the mixture was dried over magnesium sulfate and concentrated to obtain 3.2 g (35.9%) 1,1,1-trichloro-2-nitroethane.

EXAMPLE 17

To a mixture of 67.7 g (0.65 mol) of 35% hydrochloric acid and 60.7 g (0.65 mol) of 67.5% nitric acid was added 50 ml of chloroform. Then 48.9 g (0.5 mol) of 1,1-dichloroethylene were dropwise added at 22°–28.5° C. with stirring and one continued to stir for an hour at 22°–24° C. The separated chloroform layer was washed with water, dried over magnesium sulfate and concentrated to obtain 64.4 g (72.2%) of 1,1,1-trichloro-2-nitroethane.

EXAMPLE 18

To a mixture of 36.46 g (0.30 mol) of 30% hydrochloric acid and 37.81 g (0.30 mol) of 50% nitric acid was dropwise added 19.39 g (0.20 mol) of 1,1-dichloroethylene at 25° C. with stirring. After stirring for 4 hours at 25°–30° C., the separated organic layer was washed with water, dried over magnesium sulfate and concentrated to obtain 18.6 g (52.2%) of 1,1,1-trichloro-2-nitroethane.

EXAMPLE 19

To a solution of 2.10 g (0.0118 mol) of 1,1,1-trichloro-2-nitroethane in 15 ml of chloroform was dropwise added a solution of 2.75 g (0.026 mol) sodium carbonate in 15 ml of water at 2° C. with stirring, followed by addition of 1.57 g (0.01 mol) of N-(6-chloro-3-pyridyl)-methyl-N-methylamine. After stirring for 30 minutes, 3.79 g (0.042 mol) of 50% dimethylamine were dropwise added to the reaction mixture at 2° C. and stirred for 30 minutes under ice-cooling and for 30 minutes at room temperature. The separated aqueous layer was extracted with chloroform. The chloroform layer was dried over magnesium sulfate and concentrated. 4 ml of ethyl acetate were added to the residue and the mixture was ice-cooled to yield the precipitate of yellow crystals of 1-[N-(6-chloro-3-pyridyl)methyl-N-methyl-]amino-1-dimethylamino-2nitroethylene. Yield: 2.37 g (87.5%). mp. 110°–112° C.

EXAMPLE 20

The method of Example 19 was repeated by using 40% methylamine instead of dimethylamine, thereby affording 1.98 g (77.1%) of 1-[N-6-chloro-3-pyridyl)-methyl-N-methyl]amino-1-methylamino-2-nitroethylene as pale yellowish crystals. mp. 103°–104° C.

EXAMPLE 21

To a solution of 2.10 g (0.0118 mol) of 1,1,1-trichloro-2-nitroethane in 30 ml of tetrahydrofuran was dropwise added a solution of 1.2 g (0.0118 mol) of triethylamine in 2 ml of tetrahydrofuran under cooling to 0° C. and with stirring. To the mixture which was stirred for 30 minutes was dropwise added a solution of 0.99 g (0.011 mol) of 50% dimethylamine and 2.4 g (0.0237 mol) of triethylamine in 5 ml of tetrahydrofuran at −43° C.–−38° C. The mixture was stirred for 30 minutes at the same temperature and 1.0 g (0.007 mol) of 6-chloro-3-pyridyl-methylamine was dropwise added. The mixture was allowed to stand until rising to room temperature, stirred for 30 minutes and then filtered. The filtrate was concentrated, and 1,2-dichloroethane was added to the residue. The mixture was again filtered to remove insoluble substance. The filtrate was concentrated and the residue was purified by silica gel column chromatography using acetone to obtain 1.46 g (81.0%) of 1-(6-chloro-3-pyridylmethyl)amino-1-dimethylamino-2-nitroethylene as yellow crystals. mp. 124°–125° C.

EXAMPLE 22

The method of Example 21 was repeated by using 2-chloro-5-thiazolylmethylamine instead of 6-chloro-3-pyridylmethylamine, to obtain 1-(2-chloro-5-thiazolyl-methyl)amino-1-dimethylamino-2-nitroethylene as yellow crystals. Yield:76.4% mp. 101°–102° C.

EXAMPLE 23

(1) To a mixture of 4,840 g (46.46 mol) of 35% hydrochloric acid and 4,337 g (46.46 mol) of 67.5% hydrochloric acid was dropwise and with stirring added 3,500 g of 1,1-dichloroethylene (purity: 99%) at 22°–30° C., over 2.5 hours. The mixture was continued to stir for an hour and the separated lower layer was washed with 2.5l of water to obtain 5,097.3 g (79.9%) of crude 1,1,1-trichloro-2-nitroethane.

(2) 20.16 g of the above crude product were dissolved in 114 ml of chloroform and to the resulting solution was added a solution of 26.34 g (0.2486 mol) of sodium carbonate in 114 ml of water at 2°–7° C. with stirring. Then, 13.5 g (0.0791 mol) of N-(6-chloro-3-pyridyl)-methyl-N-ethylamine were dropwise added to the mixture at 5°–6° C. and stirred for 40 minutes. Further, 31.59 g (0.407 mol) of 40% methylamine were dropwise added to the mixture at 3°–7° C., followed by stirring for 30 minutes under ice-cooling and 30 minutes at room temperature. The separated aqueous layer was extracted with 48 ml of chloroform. The combined chloroform layers were concentrated, and the residue to which 39 ml of ethyl acetate were added was ice-cooled to precipitate pale yellowish crystals of 1-[N-(6-chloro-3-pyridyl)methyl-N-ethyl]amino-1-methylamino-2-nitroethylene. Yield: 18.15 g (84.9%). mp. 83°–84° C.

EXAMPLE 24

To a solution of 5.53 g (0.031 mol) of 1,1,1-trichloro-2-nitroethane in 38 ml of chloroform was dropwise added 4.5 g (0.026 mol) of N-(6-chloro-3-pyridyl)methyl-N-ethylamine under ice-cooling and with stirring. After 10 minutes, a solution of 7.23 g (0.068 mol) of sodium carbonate in 38 ml of water and after further 15 minutes, 8.67 g (0.112 mol) of 40% methylamine aqueous solution were dropwise added to the reaction mixture, followed by stirring for 25 minutes under ice-cooling and for 40 minutes at room temperature. By treating the mixture in the same way as in Example 23, 4.42 g (61.9%) of pale yellowish crystals were obtained and this product was coincided with that of Example 23.

EXAMPLE 25

To a solution of 5.53 g (0.031 mol) of 1,1,1-trichloro-2-nitroethane in 65 ml of acetonitrile was dropwise added a solution of 4.5 g (0,026 mol) of N-(6-chloro-3-pyridyl)methyl-N-ethylamine and 5.87 g (0.058 mol) of triethylamine in 15 ml of acetonitrile under ice-cooling and with stirring. After 20 minutes, 8.67 g (0,112 mol) of 40% methylamine aqueous solution were dropwise added to the reaction mixture, followed by stirring for 30 minutes under ice-cooling and for 30 minutes at room temperature. The reaction mixture was concentrated under reduced pressure. To the residue were added 30 ml of water and 50 ml of chloroform, followed by shaking well. The collected aqueous layer was extracted with 30 ml of chloroform. The combined chloroform layers were concentrated, and the residue was purified by silica gel column chromatography using chloroform-:methanol (5:1). The product was crystallized from ethyl acetate to obtain 3.5 g (48.9%) of pale yellowish crystals. The crystals were coincided with the product of Example 23.

EXAMPLE 26

To a solution of 2.05 g (0.0193 mol) of sodium carbonate in 20 ml of water were added 2.5 g (0.0176 mol) of 1,1-dichloro-2-nitroethylene and 25 ml of chloroform under ice-cooling and with stirring. To the resulting mixture was dropwise added 2.7 g (0.0158 mol) of N-(6-chloro-3-pyridyl)methyl-N-ethylamine at 3°–5° C., taking 30 minutes. To the mixture which was stirred for 30 minutes was dropwise added 4.8 g (0.0618 mol) of 40% methylamine aqueous solution at 6°–10° C. Then, the mixture was continued to be stirred for 10 minutes at the same temperature and for an hour at room temperature. The separated aqueous layer was extracted with chloroform, and the combined chloroform layers were concentrated. The residue to which 3 ml of ethyl acetate were added was allowed to stand overnight at room temperature, to precipitate crystals. The crystals as collected by filtration were washed with ethyl acetate to obtain 3.52 g (82.2%) of pale yellowish crystals which were identical with the product of Example 23.

EXAMPLE 27

To a solution of 2.5 g (0.0176 mol) of 1,1-dichloro-2-nitroethylene in 25 ml of chloroform was dropwise added 2.7 g (0.0158 mol) of N-(6-chloro-3-pyridyl)-methyl-N-ethylamine under ice-cooling and with stirring. To the mixture which was stirred for an hour was dropwise added a solution of 2.05 g (0.0193 mol) of sodium carbonate in 20 ml of water. After 30 minutes, 4.8 g (0.0618 mol) of 40% methylamine aqueous solution were dropwise added to the mixture at 6°–10° C., followed by stirring for an hour at room temperature. The separated aqueous layer was extracted with chloroform. The combined chloroform layers were concentrated, and 3 ml of ethyl acetate were added to the residue to yield crystals. The crystals collected by filtration were 3.09 g (72.2%), which were identical with the product of Example 23.

The compounds shown in the Table 1 were obtained according to the methods described in Example 10–12 or Examples 19–27.

This invention made it possible to produce 1,1,1-trihalogeno-2-nitroethanes at high yield by using the starting materials, which are less expensive and easy to handle, and to have solved all the existing problems. This invention provides a safety and low cost processes for the production of useful insecticidal α-unsaturated-amines in the agricultural field.

It is claimed:

1. A process for the production of 1,1,1-trichloro-2-nitroethane which comprises reacting vinylidene chloride $$Cl_2C=CH_2 \qquad (I)$$

with 60 to 70% nitric acid and 25 to 36% hydrochloric acid at a temperature of from 10° C. to 35° C. in an open system to yield said 1,1,1-trichloro-2-nitroethane $$Cl_3CCH_2NO_2 \qquad (II)$$

wherein each of said nitric acid and said hydrochloric acid is used in an amount of 1.2 to 1.5 equivalents to said vinylidene chloride.

* * * * *